(12) United States Patent
Samain

(10) Patent No.: US 6,368,360 B2
(45) Date of Patent: *Apr. 9, 2002

(54) METHOD FOR DYEING KERATIN FIBRES WITH A DYE COMPOSITION CONTAINING AT LEAST ONE DIRECT DYE AND A LEAST ONE BASIFYING AGENT

(75) Inventor: Henri Samain, Bievres (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/389,477

(22) Filed: Sep. 3, 1999

Related U.S. Application Data

(63) Continuation of application No. 09/080,226, filed on May 18, 1998, now Pat. No. 5,980,587, which is a continuation of application No. 08/757,274, filed on Dec. 2, 1996, now abandoned.

(30) Foreign Application Priority Data

Dec. 1, 1995 (FR) ............................................. 95-14469

(51) Int. Cl.⁷ ................................................. A61K 7/13
(52) U.S. Cl. ................................... 8/426; 8/431; 8/654
(58) Field of Search ........................... 8/405, 426, 431, 8/568, 573, 654, 655, 657, 659, 662, 407, 606

(56) References Cited

U.S. PATENT DOCUMENTS

| | | | |
|---|---|---|---|
| 3,869,454 A | 3/1975 | Lang et al. | 8/405 |
| 3,955,918 A | 5/1976 | Lang et al. | 8/426 |
| 3,985,499 A | 10/1976 | Lang et al. | 8/426 |
| 4,025,301 A | 5/1977 | Lang | 8/426 |
| 4,425,132 A | 1/1984 | Grollier et al. | 8/405 |
| 4,834,768 A * | 5/1989 | Grollier | 8/405 |
| 5,474,578 A | 12/1995 | Chan et al. | 8/426 |

FOREIGN PATENT DOCUMENTS

| | | | |
|---|---|---|---|
| GB | 909700 | * | 10/1962 |
| GB | 1174816 | | 12/1969 |
| JP | 55-022638 | | 2/1980 |
| JP | 6-184957 | | 6/1994 |
| JP | 6-271435 | | 9/1994 |
| WO | WO 95/01772 | | 1/1995 |
| WO | WO 95/15144 | | 6/1995 |

OTHER PUBLICATIONS

International Cosmetic Ingredient Dictionary, Fifth Edition, vol. 1, pp. 51–53, 1993 (No month available).*

"Chemistry of hair colorant processes—Science as an aid to formulation and development," J. Soc. Cosmet. 297, Oct. 1984.

English language translation of JP 6–271,435, Takara Belmont, pp. 1–20 (9/94).

Colour Index, Third Edition, vol. 4, pp. 4400, 4412, 4391, 4420, 4438 and 4439 (1971) (No month available).

ACS Registry No. 6359–50–8 (1998) (No month available).

* cited by examiner

*Primary Examiner*—Margaret Einsmann
(74) *Attorney, Agent, or Firm*—Finnegan, Henderson, Farabow, Garrett & Dunner, L.L.P.

(57) ABSTRACT

A dye composition for keratin fibres comprising, at least one direct dye to be mixed at the time of use, at a basic pH, with an oxidizing agent, and characterized in that it has a basic pH and in that it contains, as direct dye, at least one dye containing an optionally delocalizable quaternized nitrogen atom and a -Z=N- bond in which Z denotes a nitrogen atom or a -CH- radical. The use of the composition and the multi-compartment dyeing kits, for the dyeing of keratin fibres, in particular the hair and more particularly human hair, are also discussed.

23 Claims, No Drawings

METHOD FOR DYEING KERATIN FIBRES WITH A DYE COMPOSITION CONTAINING AT LEAST ONE DIRECT DYE AND A LEAST ONE BASIFYING AGENT

This application is a continuation application of application Ser. No. 09/080,226, filed May 18, 1998, now U.S. Pat. No. 5,980,587; which is a continuation application of application Ser. No. 08/757,274, filed Dec. 2, 1996, now abandoned, all of which are explicitly incorporated herein by reference.

The present invention relates to a dye composition, in particular a lightening dye composition, for keratin fibers, and in particular human keratin fibers, comprising at least one direct dye chosen from the group formed by dyes containing an optionally delocalizable quaternized nitrogen atom and a —Z=N— bond, in which Z denotes a nitrogen atom or a —CH— radical. The invention also relates to the use of such a composition in the above-mentioned application.

It is known to dye keratin fibers, and in particular human hair, with dye compositions containing direct dyes according to a so-called "direct dyeing" process. This process involves applying to the keratin fibers dye molecules that have an affinity for the fibers, leaving the fibres to stand, and then rinsing the fibers. This process allows shading of the color of the keratin fibers to be obtained. It is also known to dye keratin fibers, and in particular human hair, with dye compositions containing oxidation dye precursors (ortho- or para-phenylenediamines and ortho- or para-aminophenols, generally referred to as "oxidation bases") and couplers (meta-phenylenediamines, meta-aminophenols and meta-diphenols, also referred to as color modifiers, which allow the "base" colors obtained by the condensation products of the oxidation bases to be modified and enriched with glints), according to a so-called "oxidation dyeing" process.

The oxidation dyeing process usually involves lightening, that is to say that it involves applying to the keratin fibers, at basic pH, a mixture of bases and couplers and aqueous hydrogen peroxide solution, leaving the applied mixture to stand on the hair and then rinsing the hair. It allows, particularly in the case of hair dyeing, the melanin to be lightened and the hair to be dyed.

Lightening the melanin has the advantageous effect of creating a unified coloration in the case of grey hair, and, in the case of naturally pigmented hair, of bringing out the color, that is to say of making it more visible.

An oxidizing agent and, in particular, an aqueous hydrogen peroxide solution, and a basifying agent are used to obtain this lightening. A lightening of the melanin ranging from ¾ of a tone to more than 2 tones can be brought about as a function of the concentrations of aqueous hydrogen peroxide and of basifying agent, and also as a function of the nature of the basifying agent. In the case of gentle lightenings, the desired lightening is obtained in the course of superpositions.

In the so-called oxidation dyeing of hair, the use of oxidation bases sometimes leads to problems of sensitization of the scalp. In this case, if it is nevertheless desired to dye the hair, it is then possible only to use direct dyeing, with its drawbacks, in particular that of no longer obtaining the tinting effects of oxidation dyeing since conventional direct dyeing is, by itself, not lightening.

It has already been attempted in the past to obtain lightening dyes, by replacing the oxidation bases and the couplers with direct dyes. However, all the results obtained were less than optimal.

Accordingly, it was proposed to dye the hair with dye compositions based on nitro direct dyes and/or dispersed azo dyes and ammoniacal aqueous hydrogen peroxide (see in this respect French patent no. FR-1,584,965 and Japanese patent no. JP-062,711,435) by applying to the hair a mixture of the dyes and the oxidizing agent, which is prepared just before use. However, the colorations obtained did not prove to be sufficiently fast and disappeared on shampooing, allowing the lightening of the hair fibre to emerge. Such a coloration becomes aesthetically unpleasant by changing over time.

It has also been proposed to dye the hair with compositions based on cationic direct dyes of oxazine type and ammoniacal aqueous hydrogen peroxide (see in this respect Japanese patents JP-53 95693 and JP-55 022638) by applying to the hair, in a first step, ammoniacal aqueous hydrogen peroxide, and then, in a second step, a composition based on the oxazine direct dye. The coloration obtained is not satisfactory, on account of the fact that it requires a process which is made too slow by the standing times of the two successive steps. If, moreover, a mixture, prepared at the time of use, of the oxazine direct dye with ammoniacal aqueous hydrogen peroxide is applied to the hair, the hair fibre is not dyed or, at best, a coloration which is virtually nonexistent is obtained.

Moreover, the Inventor has performed tests to dye the hair with dye compositions based on anionic sulfonic dyes (which are themselves reputed for the excellent fastness) and on ammoniacal aqueous hydrogen peroxide, by applying to the hair a mixture of the dyes and the oxidizing agent, which is prepared just before use. However, in this case, no coloration of the hair fibre was observed.

Now, after considerable research has been conducted in this direction, the Inventor has discovered that it is possible to obtain dyes, in particular lightening dyes, with specific and suitably selected direct dyes, which are fast, homogenous and do not change on washing, by using a mixture which is prepared at the time of use, at basic pH, of an oxidizing agent and at least one direct dye which is chosen from those containing both an optionally delocalizable quaternized nitrogen atom and a —Z=N— bond, in which Z denotes a nitrogen atom or a —CH— radical. This discovery forms the basis of the present invention.

One subject of the present invention is thus a dye composition, in particular a lightening dye composition, for keratin fibers, and in particular for human keratin fibers such as the hair, of the type comprising, in a medium which is suitable for dyeing, at least one direct dye to be mixed at the time or use, at basic pH, with an oxidizing composition, and which is characterized in that it has a basic pH and in that it contains, as the direct dye, at least one dye containing an optionally delocalizable quaternized nitrogen atom and a —Z=N— bond in which Z denotes a nitrogen atom or a —CH— radical.

The dyes used in accordance with the present invention make it possible to achieve homogenous and fast colorations which remain aesthetic over time, since they do not change either over time or on washing. They are furthermore produced very rapidly, and in particular in a standing time of the dye/oxidizing agent mixture of five minutes. In addition, they communicate an especially shiny appearance and a natural feel without overloading, in particular on hair fibers.

Another subject of the present invention relates to a process for dyeing, and in particular lightening, keratin fibers, in particular human keratin fibers such as the hair, which involves applying to those fibers at least one composition (A) containing, in a medium which is suitable for dyeing, at least one direct dye containing an optionally delocalizable quaternized nitrogen atom and a —Z=N— bond in which Z denotes a nitrogen atom or a —CH— radical, the lightening being ensured, at basic pH, using an oxidizing agent which is mixed with the composition (A) just prior to use, or which is present in a separate composition (B) that is applied simultaneously.

Another subject of the invention is multi-compartment dyeing devices or "kits", the first compartment of which contains at least one direct dye containing an optionally delocalizable quaternized nitrogen atom and a —Z=N— bond in which Z denotes a nitrogen atom or a —CH— radical, as well as a basifying agent, and the second compartment of which contains an oxidizing agent. Another alternative "kit" is composed of a first compartment containing at least one direct dye as mentioned above, a second compartment containing a basifying agent and a third compartment containing an oxidizing agent.

The invention also relates to a "ready-to-use composition", characterized in that it contains, in a medium which is suitable for dyeing, at least one direct dye containing an optionally delocalizable quaternized nitrogen atom and a —Z=N— bond, in which Z denotes a nitrogen atom or a —CH— radical, an oxidizing agent and also, if necessary, a basifying agent in an amount which is sufficient to adjust the final pH to a value above 7, and preferably to a value ranging from 8.5 to 11.

However, other characteristics, aspects, subjects and advantages of the invention will emerge even more clearly on reading the description and the examples which follow.

The direct dyes containing an optionally delocalizable quaternized nitrogen atom and a —Z=N— bond, in which Z denotes a nitrogen atom or a —CH— radical, which may be used according to the invention are preferably chosen from the compounds of formula (I) below:

(I)

in which Z denotes a nitrogen atom or a —CH— radical. A and B each independently denote an optionally substituted benzenic or heterocyclic aromatic group, wherein each of the aromatic groups is optionally substituted on any ring atom, including the ring atom bound to the Z or N moiety of formula (I). The aromatic groups are preferably substituted with one or more halogen atoms or with one or more radicals such as a methyl radical, a phenyl radical, an $NR_1R_2$ radical or an $OR_1$ radical, in which $R_1$ and $R_2$, simultaneously or independently of each other, represent hydrogen, a $C_1$–$C_8$ alkyl radical, a $C_1$–$C_8$ hydroxyalkyl radical or a phenyl radical. X denotes an anion, preferably chloride or methyl sulphate, it being possible for the cationic charge to form an integral part of the aromatic ring or to be carried by one of its substituents.

These dyes are well known in the prior art and are described in patent applications WO-95/01772 and WO-95/15144, the disclosures of which are incorporated herein by reference. The most important cationic dyes include basic Yellow 57, Basic Red 76, Basic Brown 16, and Basic Brown 17.

Among the compounds of formula (I) which can be used in the context of the present invention, and whose cationic charge is carried by a substituent on one of the aromatic rings, it is preferred to use the compounds of the following formulae:

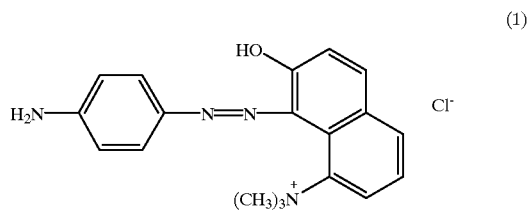

i.e., 4-aminophenylazo-2-hydroxy-8-trimethylammonio-naphthalene chloride;

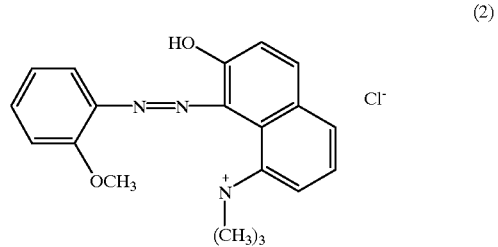

i.e., 2-methoxyphenylaze-2-hydroxy-8-trimethylammonionaphthalene chloride;

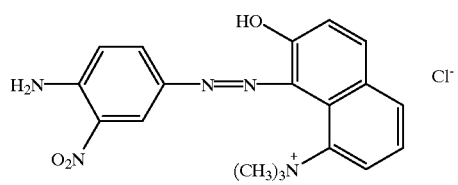

i.e., 4-amino-3-nitrophenylazo-2-hydroxy-8-trimethylammonio-naphthalene chloride; and

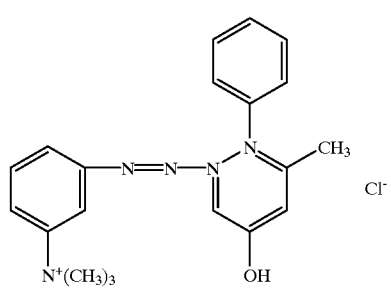

i.e., 8-trimethylammoniophenylazo-N-phenyl-3methyl-5-hydroxy-pyridazine chloride.

According to the present invention, it is even more preferred to use compounds of formula (I) whose cationic charge forms an integral part of one of the aromatic rings. Among the compounds that may be mentioned, by way of non-limiting examples, are the compounds of the following formulae:

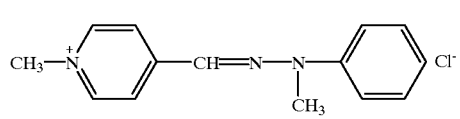

i.e., (1-methyl-1-phenyl)-2 (1-methine-4N-methylpyrdinylium] hydrazine chloride;

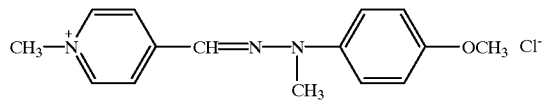

i.e. (1-methyl-1-paramethoxyphenyl)-2-(1-methine-4N-methylpyridinylium) hydrazine chloride;

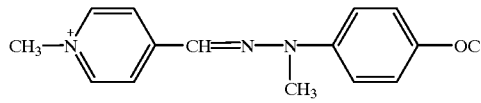

i.e. (1-methyl-1-paramethoxyphenyl)-2-(1-methine-4N-methylpyridinylium) hydrazine methylsulphate;

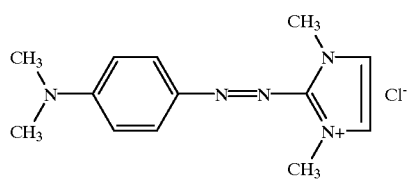

i.e., 4-dimethylaminophenylazo-2N-methyl-5N-methylimidazolylium chloride

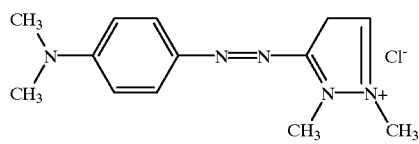

i.e., 4-dimethylaminophenylazo-2N-methyl-3N-methylimidazolyium chloride;

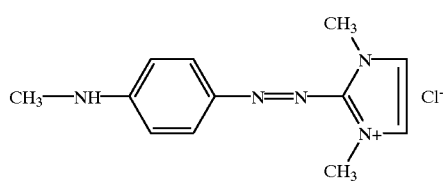

i.e., 1-methylaminophenylazo-2N-methyl-5N-methylimidazolylium chloride;

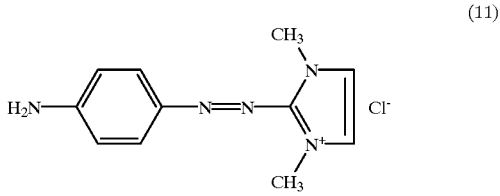

i.e., 4-aminophenylaze-2N-methyl-5N-methylimidazolylium chloride;

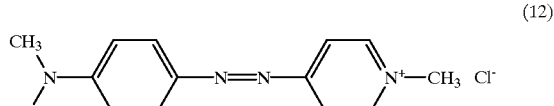

i.e., 4-dimethylaminophenylazo-4N-methyl-pyridinylium chloride; and

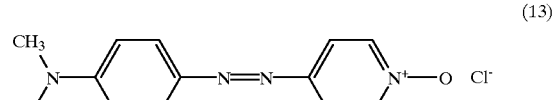

i.e., 4-dimethylaminophenylazo-4N-oxido-pyridinylium chloride.

The concentration of direct dye(s) of formula (I) preferably ranges from 0.001 to 5% by weight approximately relative to the total weight of the dye composition before it is mixed with the oxidizing agent, and more preferably ranges from approximately 0.05 to 2%.

The oxidizing agent is preferably chosen from hydrogen peroxide, urea peroxide, alkali metal bromates and persalts such as perborates and persulphates. The use of hydrogen peroxide is particularly preferred.

The pH of composition (A) which contains at least one direct dye of formula (I) as well as that of composition (B) containing the oxidizing agent as defined above are such that after mixing composition (A) with composition (B), the pH of the composition applied to the human keratin fibers is preferably above 7, and more preferably ranges from 8.5 to 11. The pH is preferably adjusted to the chosen value using basifying agents, or possibly acidifying agents, which are well known in the state of the art in the dyeing of keratin fibers.

Basifying agents which may be mentioned are aqueous ammonia, alkaline carbonates, alkanolamines, for example mono-, di- and triethanolamines and derivatives thereof, sodium hydroxide, potassium hydroxide and compounds of formula (II):

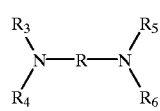

in which R is a propylene residue optionally substituted with a hydroxyl group of a $C_1$–$C_4$ alkyl radical, $R_3$, $R_4$, $R_5$, and $R_6$, simultaneously or independently of each other, represent a hydrogen atom, a $C_1$–$C_4$ alkyl radical or a $C_1$—$C_4$ hydroxyalkyl radical.

The acidifying agents are conventionally inorganic acids such as, for example, hydrochloric acid, tartaric acid, citric acid and phosphoric acid.

The oxidizing composition (B) preferably comprises an aqueous hydrogen peroxide solution whose titre may range, more particularly, from 5 to 40 volumes approximately.

The basifying agent is preferably chosen from alkanolamines when moderate lightening is required, and it is more particularly represented by aqueous ammonia when more pronounced lightening is desired.

The medium suitable for dyeing is preferably an aqueous medium comprising water and more-preferably a water/solvent(s) mixture, the solvent(s) being chosen from organic solvents such as 2-butoxyethanol or ethanol.

According to a preferred embodiment of the dyeing process of the invention, the dye composition (A) described above containing a basifying agent, and more particularly an aqueous solution of ammonia or of alkanolamine described above, is mixed, at the time of use, with an oxidizing solution in an amount which is sufficient to give rise to lightening of the melanin. The mixture obtained is then applied to human keratin fibers and is left standing on them preferably for 1 to 45 minutes, more preferably for 4 to 20 minutes, after which the fibers are rinsed, optionally washed with shampoo, rinsed again and dried.

The dye compositions according to the invention also contain, in their preferred embodiments, surfactants which are well known in the art, in proportions ranging from approximately 0.5 to 55% by weight, and preferably from 2 to 50% by weight relative to the total weight of the composition, organic solvents, in proportions ranging from approximately 1 to 40% by weight, and in particular from 5 to 30% by weight relative to the total weight of the composition, or any other cosmetically acceptable adjuvant known in the prior art in the oxidation dyeing of hair.

The composition applied to the hair may be in various forms, such as in liquid, cream or gel form, or in any other form which is suitable for dyeing keratin fibers, and in particular human hair. In particular, it may be packaged under pressure in an aerosol can in the presence of a propellant and may form a foam.

Concrete examples illustrating the invention will now be given. These examples are not intended to limit the subject matter of the invention.

EXAMPLES

EXAMPLE 1:

0.5% by weight of each of the following seven direct dyes was introduced into 10% by weight of a 20% aqueous ammonia solution, followed by addition of 100% by weight of 20-volumes aqueous hydrogen peroxide.

Each of the seven compositions obtained above was then applied to locks of European, non-permanent-waved hair containing 90% white hairs, and the compositions were allowed to remain on the hair for 30 minutes. After rinsing the locks with running water, followed by drying, the coloration obtained was graded on a scale from 0 to 3, as follows:

Grade 0 - no coloration

Grade 1 - slightly perceptible but unacceptable coloration

Grade 2 - clearly perceptible coloration but at the limit of acceptability

Grade 3 - good coloration.

The results obtained were as follows:

Dyes not according to the invention:

anionic sulfonic dye:

Acid Black 1 (C.l.20470)→grade=0 nitrobenzene dye:

N1, N4, N4-tris(β-hydroxyethyl)-1,4-diamino 2-nitrobenzene→grade=1 cationic dye of oxazine type:

Basic Blue 3→grade=0 cationic dye containing no —N=N or —CH=N— function:

1-(N-methylmorpholiniumpropylamino)-4-hydroxyanthraquinone (methyl sulphate)→grade=0

Dyes according to the invention (the Nos. correspond to the products in the description):

dye (8) with an —N=N— function→grade=3 dye (6) with a —CH=N— function→grade=3

Consequently, among the seven direct dyes studied, only the dyes according to the invention make it possible to obtain good lightening colorations.

EXAMPLE 2:

The following dye compositions were prepared:

Direct dye of formula (I) according to the invention* . . . xg

20% aqueous ammonia solution . . . 10 g

Demineralized water . . . q.s. for 100 g * See Table (I) following page, the Nos. corresponding to the products in the description.

In a first experiment (lightening dye according to the invention), locks of natural chestnut brown European hair were dyed with a mixture, prepared at the time of use, of the composition described above with its weight of 20-volumes aqueous hydrogen peroxide. After allowing the composition to remain on the locks for 5 minutes, they were rinsed with running water and then dried.

In a second experiment (comparative standard direct dyeing), other locks of hair (same quality as above) were separately dyed with a composition as described above, the only difference being that it contained no aqueous hydrogen peroxide. After allowing the composition to remain on the locks for the same length of time as for the above dyeing, they were rinsed and then dried.

The lightening dyes according to the invention were thus compared with corresponding standard direct dyes, this being with the direct dyes (8), (10) and (10)+(7) of formula (I) according to the invention.

The compared shades were measured in terms of L, a, b values (color notation system in which (L) denotes the intensity, (a) denotes the shade and (b) denotes the purity) on a Minolta CM2002 colorimeter.

TABLE (I)

| Dyeing with dye No. | L, a, b | L | a | b | Comments |
|---|---|---|---|---|---|
| (8): 2 g | invention | 22.44 | 6.30 | 1.52 | a increases → redder shade |
| | comparative | 22.31 | 3.88 | 0.68 | |
| (10): 0.4 g + (7): 1.8 g | invention | 23.74 | 5.35 | 3.96 | a and b increase → more orange shade |
| | comparative | 22.63 | 2.39 | 1.90 | |
| (10): 2 g | invention | 22.60 | 6.67 | 2.53 | a increases → redder shade |
| | comparative | 22.21 | 3.83 | 1.33 | |
| control (no dye) | | 22.62 | 1.84 | 2.06 | |

These results demonstrate that the lightening dyeing using the direct dyes according to the invention (with aqueous hydrogen peroxide) had better performance in terms of visual effect (generated more visible colorations) than standard direct dyeing with these same dyes (without aqueous hydrogen peroxide).

These lightening dyeings gave colorations that were moreover homogeneous, fast and shiny and which remained aesthetically attractive over time. The hair also offered a natural appearance without overloading.

I claim:

1. A method for dyeing a keratin fiber, comprising applying to said fiber a dye composition in an amount sufficient to dye said fiber, wherein said dye composition comprises, in a medium suitable for dyeing, at least one direct dye and at least one basifying agent in an amount sufficient to adjust the pH of said composition to a basic value, while simultaneously applying to said fiber at least one oxidizing agent whereby said at least one oxidizing agent is mixed with said dye composition, wherein said at least one direct dye is chosen from:

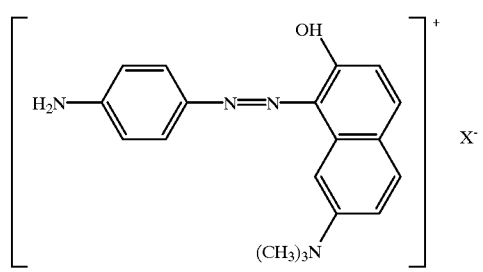

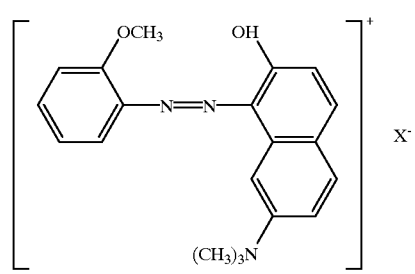

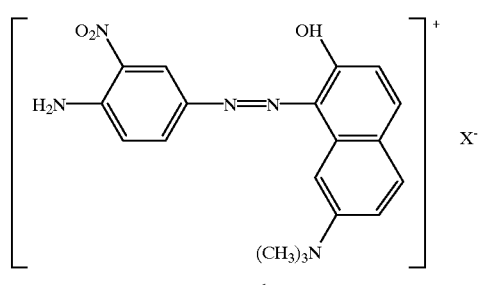

and

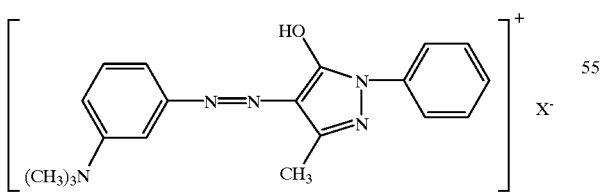

wherein X⁻ is an anion.

2. A method according to claim 1, wherein said dye composition comprises said at least one oxidizing agent.

3. A method according to claim 1, wherein said at least one oxidizing agent is present in a composition separate from said dye composition.

4. A method according to claim 1, wherein X⁻ is chosen from a chloride anion and a methyl sulphate anion.

5. A method according to claim 1, wherein said at least one direct dye is present in a concentration ranging from 0.001 to 5% by weight relative to the total weight of said dye composition before it is mixed with said at least one oxidizing agent.

6. A method according to claim 5, wherein said at least one direct dye is present in a concentration ranging from 0.05 to 2% by weight relative to the total weight of said dye composition before it is mixed with said at least one oxidizing agent.

7. A method according to claim 1, wherein said at least one basifying agent is chosen from aqueous ammonia and alkanolamines.

8. A method according to claim 1, wherein said at least one oxidizing agent comprises aqueous hydrogen peroxide.

9. A method according to claim 1, wherein said keratin fiber is a human keratin fiber.

10. A method according to claim 9, wherein said human keratin fiber is human hair.

11. A method according to claim 1, further comprising:

allowing the mixture of said dye composition and said at least one oxidizing agent to remain on said fiber for a time sufficient to dye said fiber, and subsequently rinsing said fiber.

12. A method according to claim 11, wherein said time ranges from 1 to 45 minutes.

13. A method according to claim 12, wherein said time ranges from 4 to 20 minutes.

14. A method according to claim 1, wherein said dye composition is a lightening dye composition.

15. A method according to claim 1, wherein said at least one basifying agent is present in a an amount sufficient to adjust the pH of the mixture of said dye composition and said at least one oxidizing agent to a value ranging from 8.5 to 11.

16. A ready-to-use dye composition, comprising:

at least one direct dye containing an optionally delocalizable quaternized nitrogen atom and a —Z=N— bond, wherein Z denotes a nitrogen atom or a —CH— radical, at least one basifying agent in an amount sufficient to adjust the pH of said composition to a basic value, and at least one oxidizing agent, wherein, when Z is a nitrogen atom, said at least one direct dye is chosen from:

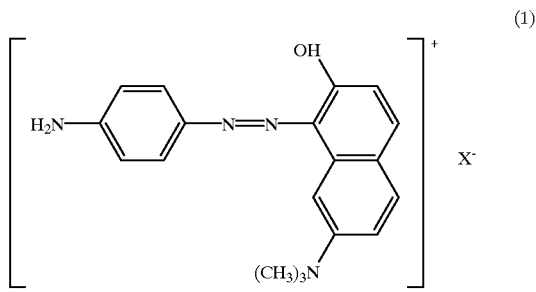

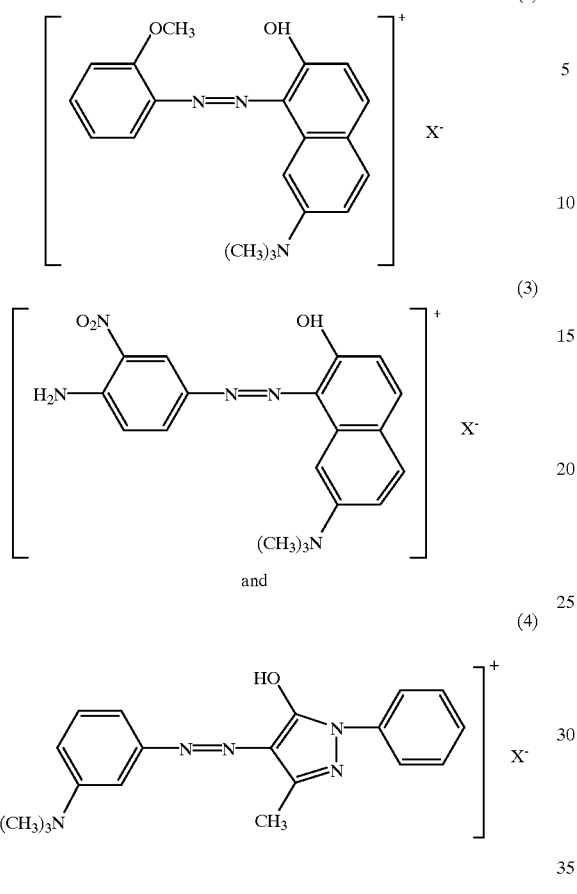

wherein X⁻ is an anion.

17. A composition according to claim 16, wherein said at least one oxidizing agent comprises aqueous hydrogen peroxide.

18. A composition according to claim 17, wherein said dye composition is a lightening dye composition.

19. A composition according to claim 18, wherein Z denotes a —CH— radical.

20. A composition according to claim 19, wherein said at least one basifying agent is present in an amount sufficient to adjust the pH of the mixture of said dye composition and said at least one oxidizing agent to a value ranging from 8.5 to 11.

21. A multi-compartment kit for the dyeing of a human keratin fiber, comprising at least two compartments, wherein one of said at least two compartments contains a dye composition comprising at least one direct dye containing an optionally delocalizable quaternized nitrogen atom and a —Z=N— bond, wherein Z denotes a nitrogen atom or a —CH— radical, and wherein another of said at least two compartments contains a composition comprising at least one oxidizing agent, and further wherein at least one basifying agent is present in a third compartment of said device or in the compartment containing said dye composition, wherein, when Z is a nitrogen atom, said at least one direct dye is chosen from:

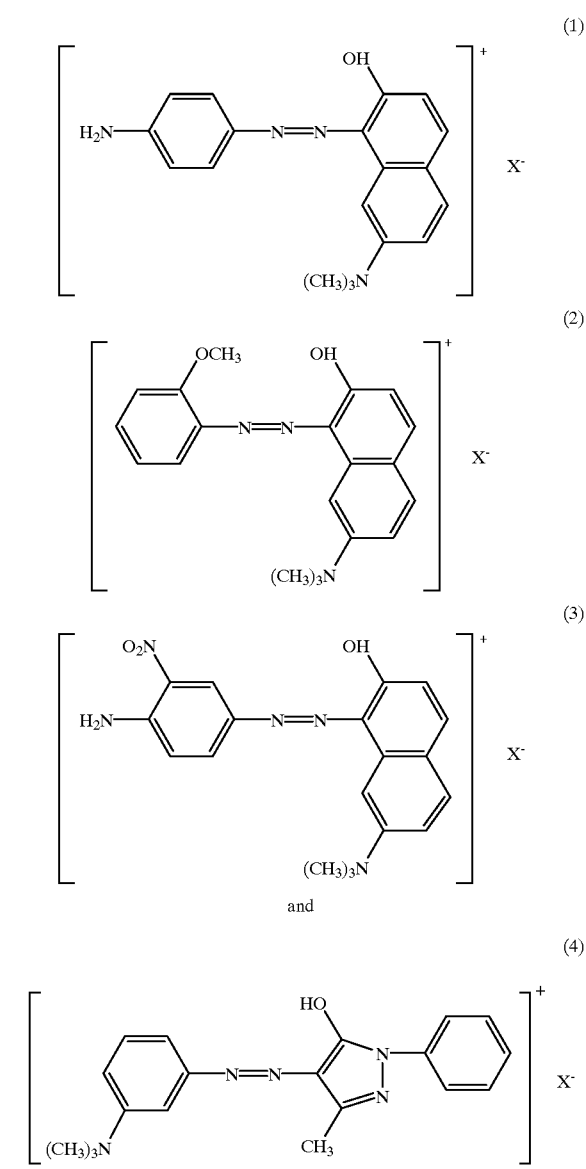

wherein X⁻ is an anion.

22. A multi-compartment kit according to claim 21, wherein Z denoted a —CH— radical.

23. A method for dyeing a keratin fiber, comprising applying to said fiber a dye composition in an amount sufficient to dye said fiber, wherein said dye composition comprising, in a medium suitable for dyeing, at least one direct dye containing an optionally delocalizable quaternized nitrogen atom and a —N=N— bond and at least one basifying agent in an amount sufficient to adjust the pH of said composition to a basic value, while simultaneously applying to said fiber at least one oxidizing agent whereby said at least one oxidizing agent is mixed with said dye composition, wherein said at least one direct dye is a compound of formula (I):
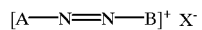 (I)
in which: A and B each independently denote an optionally substituted benzenic or heterocyclic aromatic group, and $X^-$ denotes an anion, and wherein the cationic charge is carried by one of the substituents on said aromatic groups.
* * * * *

UNITED STATES PATENT AND TRADEMARK OFFICE
CERTIFICATE OF CORRECTION

PATENT NO. : 6,368,360 B2
DATED : April 9, 2002
INVENTOR(S) : Henri Samain

It is certified that error appears in the above-identified patent and that said Letters Patent is hereby corrected as shown below:

Column 2,
Line 49, "time or use" should read -- time of use --.

Column 3,
Line 61, insert space between "16," and "and".

Column 4,
Line 14, "naphthalene" should read -- naphthalone --.

Column 8,
Line 1, "C.1." should read -- C.I. --.

Column 11,
Line 44, "claim 17" should read -- claim 16 --.
Line 47, "claim 18" should read -- claim 16 --.
Line 51, "claim 19" should read -- claim 16 --.

Signed and Sealed this

Tenth Day of September, 2002

Attest:

JAMES E. ROGAN
Attesting Officer
Director of the United States Patent and Trademark Office